United States Patent
Chugh

(10) Patent No.: US 11,627,906 B2
(45) Date of Patent: Apr. 18, 2023

(54) SYSTEM AND A METHOD FOR USING A NOVEL ELECTROCARDIOGRAPHIC SCREENING ALGORITHM FOR REDUCED LEFT VENTRICULAR EJECTION FRACTION

(71) Applicant: CEDARS-SINAI MEDICAL CENTER, Los Angeles, CA (US)

(72) Inventor: Sumeet S. Chugh, Santa Monica, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 348 days.

(21) Appl. No.: 16/605,726

(22) PCT Filed: Apr. 17, 2018

(86) PCT No.: PCT/US2018/027943
§ 371 (c)(1),
(2) Date: Oct. 16, 2019

(87) PCT Pub. No.: WO2018/195058
PCT Pub. Date: Oct. 25, 2018

(65) Prior Publication Data
US 2021/0369180 A1 Dec. 2, 2021

Related U.S. Application Data

(60) Provisional application No. 62/486,927, filed on Apr. 18, 2017.

(51) Int. Cl.
*A61B 5/366* (2021.01)
*G16H 20/40* (2018.01)
(Continued)

(52) U.S. Cl.
CPC .......... *A61B 5/366* (2021.01); *A61B 5/02028* (2013.01); *A61B 5/02438* (2013.01);
(Continued)

(58) Field of Classification Search
CPC .......... A61B 5/366; A61B 5/353; A61B 5/271; A61B 5/36; A61B 5/02028; A61B 5/02438; G16H 50/30; G16H 50/70; G16H 50/20
See application file for complete search history.

(56) References Cited

U.S. PATENT DOCUMENTS

| 7,996,070 B2 | 8/2011 | Van Dam et al. |
| 2004/0044292 A1 | 3/2004 | Yasushi et al. |

(Continued)

FOREIGN PATENT DOCUMENTS

| JP | 2020517334 A | 6/2020 |
| WO | 2006126020 A3 | 11/2006 |
| WO | 2018195058 A1 | 10/2018 |

OTHER PUBLICATIONS

Jonathan Jui, Sumeet S. Chugh, Left-ventricular geometry and risk of sudden cardiac arrest in patients with preserved or moderately reduced left-ventricular ejection fraction, EP Europace, vol. 19, Issue 7, Jul. 2017, pp. 1146-1152, https://doi.org/10.1093/europace/euw126 (Year: 2017).*

(Continued)

*Primary Examiner* — Michael W Kahelin
*Assistant Examiner* — Naveed R. Kolia
(74) *Attorney, Agent, or Firm* — Nixon Peabody LLP

(57) ABSTRACT

A system and a method for identifying a patient with a threshold number of distinct ECG abnormalities. The system and the method include an ECG monitoring device; a server; a database; a network; a memory containing machine readable medium comprising a machine executable code having (Continued)

stored thereon instructions for identifying patients with a threshold number of distinct ECG abnormalities; and a processor coupled to the memory, the processor configured to execute the machine executable code to cause the processor to: receive an ECG data output from the ECG monitoring device; process the ECG data output to identify abnormalities in the ECG data; and analyze the abnormalities in the ECG data in order to output an indication of whether the patient has depressed LVEF, wherein the ECG monitoring device, the server, the database, the memory, and the processor are coupled to the network via communication links.

18 Claims, 3 Drawing Sheets

(51) Int. Cl.
　　　*G16H 50/30*　　　(2018.01)
　　　*G16H 50/70*　　　(2018.01)
　　　*G16H 50/20*　　　(2018.01)
　　　*A61B 5/353*　　　(2021.01)
　　　*A61B 5/271*　　　(2021.01)
　　　*A61B 5/36*　　　(2021.01)
　　　*A61B 5/02*　　　(2006.01)
　　　*A61B 5/024*　　　(2006.01)
　　　*A61B 5/00*　　　(2006.01)

(52) U.S. Cl.
　　　CPC .............. *A61B 5/271* (2021.01); *A61B 5/353* (2021.01); *A61B 5/36* (2021.01); *A61B 5/7264* (2013.01); *G16H 20/40* (2018.01); *G16H 50/20* (2018.01); *G16H 50/30* (2018.01); *G16H 50/70* (2018.01); *A61B 2560/02* (2013.01)

(56) References Cited

U.S. PATENT DOCUMENTS

| | | |
|---|---|---|
| 2006/0264768 A1 | 11/2006 | Satin et al. |
| 2008/0319331 A1 | 12/2008 | Zizzo et al. |
| 2016/0100803 A1 | 4/2016 | Korzinov et al. |
| 2016/0135706 A1* | 5/2016 | Sullivan .............. A61B 5/316 600/509 |
| 2021/0369180 A1 | 12/2021 | Chugh |

OTHER PUBLICATIONS

Jonathan Jui, Sumeet S. Chugh, Tpeak-to-Tend interval corrected for heart rate: a more precise measure of increased sudden death risk?, Heart Rhythm, vol. 13, Issue 11, (Year: 2016).*

EP Extended European Search Report for EP 18788497 dated Dec. 7, 2020, 8 pages.

Suszko et al., Quantifying abnormal QRS peaks using a novel time-domain peak detection algorithm: Application in patients with cardiomyopathy at risk of sudden death, 2015 IEEE International Conference on Electro/Information Technology, May 21, 2015, pp. 20-24.

Houghton et al., Should general practitioners use the electrocardiogram to select patients with suspected heart failure for echocardiography?, International Journal of Cardiology, Elsevier, Amsterdam, NL, Oct. 31, 1997, 62 (1):31-36.

Aro et al., Electrical risk score beyond the left vertricular ejection fraction: prediction of sudden cardiac death in the Oregon Sudden Unexpected Death Study and the Atherosclerosis Risk in Communities Study, European Heart Journal, Jun. 26, 2017, 38(40):3017-3025.

JP Notice of Reason for Rejection for JP 2019-556679 dated Dec. 13, 2021, 13 pages.

International Search Report and Written Opinion for PCT/US2018/027943 dated Jul. 3, 2018, 14 pages.

* cited by examiner

SYSTEM AND A METHOD FOR USING A NOVEL ELECTROCARDIOGRAPHIC SCREENING ALGORITHM FOR REDUCED LEFT VENTRICULAR EJECTION FRACTION

CROSS-REFERENCE TO RELATED APPLICATIONS

This application is the national phase of International Application No. PCT/US2018/027943, filed Apr. 17, 2018, which designated the U.S. and that International Application was published under PCT Article 21(2) in English. This application claims priority under 35 U.S.C. § 119(e) to U.S. Provisional Application No. 62/486,927, filed Apr. 18, 2017, the contents of which are herein incorporated by reference in their entirety.

STATEMENT REGARDING FEDERALLY SPONSORED RESEARCH OR DEVELOPMENT

This invention was made with government support under Grant Nos. HL122492 and HL126938 awarded by National Institutes of Health. The government has certain rights in the invention.

FIELD OF THE INVENTION

The present disclosure generally relates to a system and a method that uses electrocardiographic (ECG) screening algorithm that screens patients for heart disease.

BACKGROUND OF THE DISCLOSURE

The prevalence of significant left ventricular (LV) systolic dysfunction in the adult population is around 2-3%. Approximately half of these subjects are asymptomatic and others may be symptomatic but undiagnosed, and unfortunately for many, sudden cardiac death (SCD) can be the first manifestation of their heart disease. Patients with severe LV dysfunction who are currently asymptomatic, could have heart failure therapy initiated at an earlier stage, making an impact on heart failure burden. Identification of a higher proportion of patients with symptomatic systolic LV dysfunction eligible for the primary prevention implantable defibrillator (ICD) will reduce underutilization of this modality, with a positive impact on SCD burden. There is a significant under-utilization of the primary prevention ICD in the general population, mainly due to low prevalence of echocardiographic screening for reduced LVEF. It is currently not feasible to broadly deploy echocardiographic screening in the community.

SUMMARY OF THE DISCLOSURE

As such, a novel, non-invasive and cost-effective methods to identify patients most likely to have severely reduced LV ejection fraction, could enhance treatment of patients with heart failure as well as the screening process to identify appropriate candidates for the primary prevention ICD.

The following embodiments and aspects thereof are described and illustrated in conjunction with systems, compositions and methods which are meant to be exemplary and illustrative, not limiting in scope.

In an aspect of the present disclosure, a system for identifying patients with a threshold number of distinct ECG abnormalities is disclosed. The system includes an ECG monitoring device; a server; a database; a memory containing machine readable medium comprising machine executable code having stored thereon instructions for performing a method disclosed herein; and a processor coupled to the memory, wherein the processor is configured to execute the machine executable code to cause the processor to: receive an ECG data output from the ECG monitoring device; process the ECG data to identify abnormalities in the ECG data; and analyze the abnormalities to output an indication of whether the patient has depressed LVEF.

In an embodiment of the present disclosure, analyzing the abnormalities may include determining whether a threshold number of abnormalities are identified.

In an embodiment of the present disclosure, analyzing the abnormalities may include weighting certain abnormalities and outputting an abnormality score.

In an embodiment of the present disclosure, the server and database may be connected to each other via at least one communication link.

The at least one ECG monitoring device and the monitor computer may be configured to be coupled to the network via communication links.

The at least one ECG monitoring device may be configured to be used by, for example, an authorized user) of a patient to whom the at least one ECG monitoring device is being used.

The at least one ECG monitoring device may be configured to collect ECG data from the patient, the data may then transferred immediately to the monitor computer, the hosted server, or the database for screening to detect medical conditions in otherwise asymptomatic patient.

The medical conditions may include left ventricular ejection fraction.

The at least one ECG device, the monitor computer, the hosted server, and the database may be configured to each include a computer-readable medium including a computer program that may be executed to carry out the processes disclosed herein.

The computer-readable medium may be configured to include a code section or code segment for performing each step disclosed herein.

The code may include an algorithm to screen (or analyze) asymptomatic patients for severally depressed LVEF using only ECG data.

The algorithm may identify patients as candidates for the primary prevention treatment of an implantable defibrillator (ICD).

The algorithm may include at least one of: probability algorithm, machine learning algorithm, or combination thereof.

The algorithm may include a step-wise logistical regression to analyze a 12-lead ECG signal for specific abnormalities (or LVEF).

The specific abnormalities may include at least one of: elevated resting Heart rate, global P-wave duration, PR interval, QRS duration, QTc interval, QRS-T angle, Intrinsicoid deflection, QRS transition zone, T-peak to T-end interval or left ventricular hypertrophy.

In another aspect of the present disclosure, a method for identifying patients with a threshold number of distinct ECG abnormalities is disclosed. The method includes: receiving, at a controller, ECG data from a ECG monitoring device on a patient; processing, by the controller, the ECG data to identify abnormalities; and outputting an indication of whether the patient has LVEF.

Another aspect of the present disclosure discloses a computer readable storage medium tangibly embodying a computer readable program code having computer readable instructions which, when implemented, cause a computer to carry out the steps as described herein.

Another aspect of the present disclosure discloses a non-transitory machine readable medium having stored thereon instructions for performing a method comprising machine executable code which when executed by at least one machine, causes the machine to carry out the steps as disclosed herein.

Yet another aspect of the present disclosure discloses a computer readable storage medium tangibly embodying a computer readable program code having computer readable instructions which, when implemented, cause a computer to carry out the steps of a method as described herein.

Embodiments

Embodiment 1. A system for identifying a patient with a threshold number of distinct ECG abnormalities comprising:
an ECG monitoring device;
a server;
a database;
a memory containing machine readable medium comprising a machine executable code having stored thereon instructions for identifying patients with a threshold number of distinct ECG abnormalities; and
a processor coupled to the memory, the processor configured to execute the machine executable code to cause the processor to:
receive an ECG data output from the ECG monitoring device;
process the ECG data output to identify abnormalities in the ECG data; and
analyze the abnormalities in the ECG data in order to output an indication of whether the patient has the distinct ECG abnormalities,
wherein the ECG monitoring device, the server, the database, the memory, and the processor are coupled to a network via communication links.

Embodiment 2. The system of embodiment 1, wherein the ECG monitoring device comprises at least one of: a ECG machine to measure 12 lead ECG, an electrode that measures 3-lead ECG, combination of 4 electrodes and 3 lead ECG with an additional 5$^{th}$ electrode located near or on the patient's chest to measure 5 lead ECG, a holter monitor test, a cardiac event recorder, a cardiac loop recorder, an implantable loop recorder, a stress ECG, a wearable device with heart monitoring capability, and a combination thereof.

Embodiment 3. The system of embodiment 1, wherein the processing of the ECG data output comprises converting a raw data into a processed data, wherein the processed data further comprises at least one of: heart rate, heart rate variability, and other forms of suitable data for analyzing the abnormalities in the ECG data.

Embodiment 4. The system of embodiment 1, wherein analyzing the abnormalities comprises determining whether a threshold or predetermined number of abnormalities are identified.

Embodiment 5. The system of embodiment 1, wherein analyzing the abnormalities comprises weighting certain abnormalities and outputting an abnormality score.

Embodiment 6. The system of embodiment 5, wherein the certain abnormalities are detected by meeting a threshold or predetermined measurement of at least one of the following factors: elevated resting Heart rate, global P-wave duration, PR interval, QRS duration, QTc interval, QRS-T angle, Intrinsicoid deflection, QRS transition zone, T-peak to T-end interval or left ventricular hypertrophy, and any combination thereof.

Embodiment 7. The system of embodiment 1, wherein the at least one ECG monitoring device, the server, the database, and the monitor computer are coupled to the network via communication links.

Embodiment 8. The system of embodiment 1, wherein the at least one ECG monitoring device is configured to be used by an authorized user of the patient to whom the at least one ECG monitoring device is being used.

Embodiment 9. The system of embodiment 1, wherein once the at least one ECG monitoring device collects ECG data from the patient and transfer the collected ECG data immediately to at least one of the following: the monitor computer, the hosted server, or the database for screening to detect medical conditions in otherwise asymptomatic patient.

Embodiment 10. The system of embodiment 9, wherein the medical conditions comprise left ventricular ejection fraction.

Embodiment 11. The system of embodiment 1, wherein the at least one ECG device, the monitor computer, the hosted server, and the database are configured to each include a computer-readable medium including a computer program that may be executed to carry out the method comprising: collecting an ECG data output from the patient; processing the collected ECG data output to identify the abnormalities in the collected ECG data; and assign abnormality scores to the collected ECG data by comparing the collected ECG data to a predetermined or threshold measurement data for the abnormalities.

Embodiment 12. The system of embodiment 11, wherein the computer-readable medium is configured to comprise a code section or code segment for performing each step disclosed in claim 10.

Embodiment 13. The system of embodiment 12, wherein the code section or code segment comprises an algorithm to screen or analyze asymptomatic patients for severally depressed LVEF using only ECG data.

Embodiment 14. The system of embodiment 13, wherein the algorithm identifies patients as candidates for the primary prevention treatment of an implantable defibrillator (ICD).

Embodiment 15. The system of embodiment 13, wherein the algorithm comprises at least one of: probability algorithm, machine learning algorithm, and a combination thereof.

Embodiment 16. The system of embodiment 13, wherein the algorithm comprises a step-wise logistical regression to analyze a 12-lead ECG signal for specific abnormalities.

Embodiment 17. The system of embodiment 16, wherein the specific abnormalities comprise at least one of: elevated resting Heart rate, global P-wave duration, PR interval, QRS duration, QTc interval, QRS-T angle, Intrinsicoid deflection, QRS transition zone, T-peak to T-end interval, left ventricular hypertrophy, and a combination thereof Embodiment 18. A method for identifying patients with a threshold number of distinct ECG abnormalities comprising:
receiving, at a controller, ECG data from a ECG monitoring device on a patient;
processing, by the controller, the ECG data to identify abnormalities; and
outputting an indication of whether the patient has LVEF.

Embodiment 19. The system of embodiment 18, wherein the ECG monitoring device is connected to a network, at least one monitoring device, a network, a monitor computer, a hosted server, and a database via communication links, wherein the ECG monitoring device, the at least one monitoring device, the monitor computer, the hosted server, and the database each comprise the controller.

Embodiment 20. The system of embodiment 19, wherein the controller comprises a non-transitory machine readable medium having stored thereon instructions for performing a method comprising machine executable code which when executed by at least one machine, causes the machine to carry out the method of identifying patients with a threshold number of distinct ECG abnormalities.

Embodiment 21. A computer-implemented method for identifying patients with a threshold number of distinct ECG abnormalities, the method comprising:

a processor configurable to execute a data processing application receiving input data from an ECG monitoring device, wherein the input data comprises a raw electrocardiogram signal, the processor processing the raw electrocardiogram signal into a processed output data, the processor aggregating the processed output data to produce a pattern of the processed output data, the processor compares the processed output data is compared against an predetermined or inputted threshold of data for distinct ECG abnormalities, and the processor comprising a computer readable program having a code section or code segment that is executed to carry out comparison between the pattern of the processed output data and the predetermined or inputted threshold of data for distinct ECG abnormalities, wherein the code section or code segment comprises an algorithm selected from at least one of: probability algorithm, machine learning algorithm, or combination thereof, wherein the algorithm further comprises using a stepwise logistic regression to carry out the comparison between the pattern of the processed output data and the predetermined or inputted threshold of data for distinct ECG abnormalities, wherein, if the processed output data is compared against the predetermined or inputted threshold of data for distinct ECG abnormalities, a first data set in the processed output data is connected to a second data set in the predetermined or inputted threshold of data for distinct ECG abnormalities based on a matching pattern of the first and the second data sets, and the first data set is assigned an abnormality score to indicate a percentage of likelihood of distinct ECG abnormalities based on the first data set's matching percentage to the second data set, and wherein the distinct ECG abnormalities comprise at least one of: elevated resting Heart rate, global P-wave duration, PR interval, QRS duration, QTc interval, QRS-T angle, Intrinsicoid deflection, QRS transition zone, T-peak to T-end interval, left ventricular hypertrophy, and a combination thereof.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION OF THE DISCLOSURE

Figure 1:
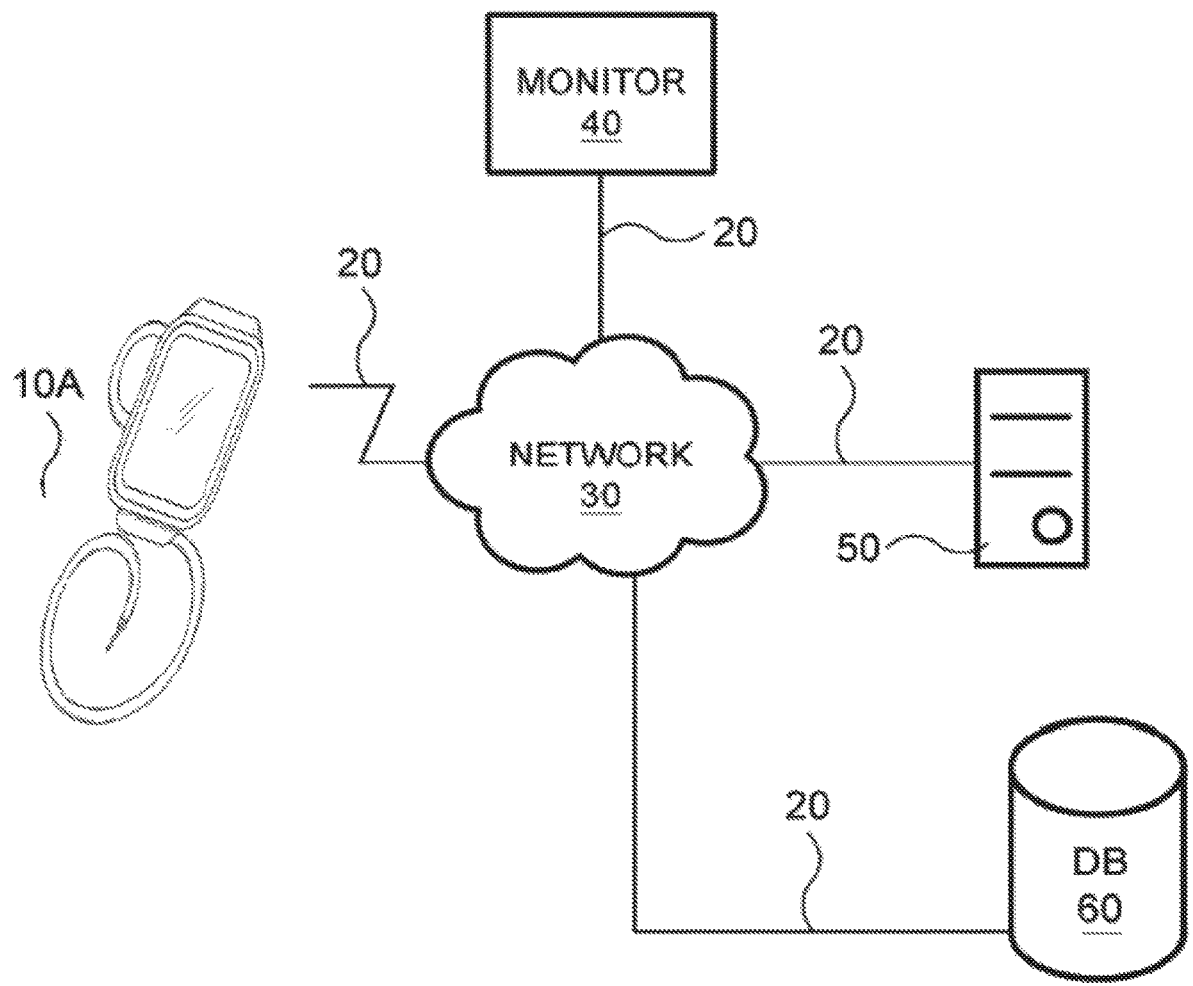
FIG. 1 shows an example of a system that identifies patients with a threshold number of distinct ECG abnormalities that is constructed in accordance with the principles of the present disclosure.

The disclosure and the various features and advantageous details thereof are explained more fully with reference to the non-limiting implementations and examples that are described and/or illustrated in the accompanying drawings and detailed in the following description. It should be noted that the features illustrated in the drawings are not necessarily drawn to scale, and features of one implementation may be employed with other implementations as any person skilled in the art would recognize, even if not explicitly stated herein. Descriptions of well-known components and processing techniques may be omitted so as to not unnecessarily obscure the implementations of the disclosure. The examples used herein are intended merely to facilitate an understanding of ways in which the disclosure may be practiced and to further enable those of skill in the art to practice the implementations of the disclosure. Accordingly, the examples and implementations herein should not be construed as limiting the scope of the disclosure.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

The terms "patient" and "subject" are used interchangeably herein. These terms are intended to include all animal subjects, including mammals. Human patients/subjects are intended to be within the scope of the patients/subjects treated using the various embodiments of the inventive systems, apparatuses and methods described herein.

A term "wireless transmitter," as used in this disclosure, means at least one of microwave, Infrared or RF module or a cellular/wireless modem and is configured to transmit data.

The term "coupled" means at least either a direct electrical connection between the connected items or an indirect connection through one or more passive or active intermediary devices. The term "circuit" means at least either a single component or a multiplicity of components, either active and/or passive, that are coupled together to provide a desired function. The term "signal" as used herein may include any meanings as may be understood by those of ordinary skill in the art, including at least an electric or magnetic representation of current, voltage, charge, temperature, data or a state of one or more memory locations as expressed on one or more transmission mediums, and generally capable of being transmitted, received, stored, compared, combined or otherwise manipulated in any equivalent manner.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a central processing unit, a general purpose computer, a cloud, a super computer, a personal computer, a laptop computer, a palmtop computer, a mobile device, a tablet computer, a notebook computer, a desktop computer, a workstation computer, a server, or the like, or an array of processors, microprocessors, central processing units, general purpose computers, super computers, personal computers, laptop computers, palmtop computers, mobile devices, tablet computers, notebook computers, desktop computers, workstation computers, servers, or the like.

A "server," as used in this disclosure, means any combination of software and/or hardware, including at least one application and/or at least one computer to perform services for connected clients as part of a client-server architecture. The at least one server application may include, but is not limited to, for example, an application program that can accept connections to service requests from clients by sending back responses to the clients. The server may be configured to run the at least one application, often under heavy workloads, unattended, for extended periods of time with minimal human direction. The server may include a plurality of computers configured, with the at least one application being divided among the computers depending upon the workload. For example, under light loading, the at least one application can run on a single computer. However, under heavy loading, multiple computers may be required to run the at least one application. The server, or any if its computers, may also be used as a workstation.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communications network," as used in this disclosure, means a wired and/or wireless medium that conveys data or information between at least two points. The wired or wireless medium may include, for example, a metallic conductor link, a radio frequency (RF) communication link, an Infrared (IR) communication link, telecommunications networks, an optical communication link, internet (wireless and wired) or the like, without limitation. The RF communication link may include, for example, WiFi, WiMAX, IEEE 802.11, DECT, 0G, 1G, 2G, 3G, 4G, 5G or future cellular standards, Bluetooth, Bluetooth Low Energy, NFC, ultrasound, induction, laser (or similar optical transmission) and the like.

A "computer-readable storage medium," as used in this disclosure, means any medium that participates in providing data (for example, instructions) which may be read by a computer. Such a medium may take many forms, including non-volatile media, volatile media, and transmission media. Non-volatile media may include, for example, optical or magnetic disks, flash memory, and other persistent memory. Volatile media may include dynamic random access memory (DRAM). Transmission media may include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read. The computer-readable medium may include a "Cloud," which includes a distribution of files across multiple (e.g., thousands of) memory caches on multiple (e.g., thousands of) computers.

Various forms of computer readable media may be involved in carrying sequences of instructions to a computer. For example, sequences of instruction (i) may be delivered from a RAM to a processor, (ii) may be carried over a wireless transmission medium, and/or (iii) may be formatted according to numerous formats, standards or protocols, including, for example, WiFi, WiMAX, IEEE 802.11, DECT, 0G, 1G, 2G, 3G or 4G cellular standards, Bluetooth, or the like.

A "network," as used in this disclosure means, but is not limited to, for example, at least one of a local area network (LAN), a wide area network (WAN), a metropolitan area network (MAN), a personal area network (PAN), a campus area network, a corporate area network, a global area network (GAN), a broadband area network (BAN), a cellular network, the Internet, the cloud network, or the like, or any combination of the foregoing, any of which may be configured to communicate data via a wireless and/or a wired communication medium. These networks may run a variety of protocols not limited to TCP/IP, IRC, SSL, TLS, UDP, or HTTP.

Overview

As disclosed herein, the present invention provides a cost-effective system and algorithm to screen asymptomatic patients for severally depressed LVEF (≤35%) using only ECG data. This disclosed system and algorithm offer a cost-effective way of sequestering the subgroup of individuals in the general population, who have a significantly high chance of having asymptomatic or un-recognized left ventricular systolic dysfunction. If identification of such individuals can be improved, such individuals can receive early treatment for heart failure, even before they become asymptomatic. Furthermore, those who are resistant to optimal medical therapy and continue to have severe left ventricular systolic dysfunction are likely to benefit from a primary prevention ICD.

FIG. 1 shows an example of a system that is constructed according to the principles of the disclosure that provides using ECG (or EKG) monitoring device to a patient, and receiving and carrying out wireless transmission of instructions, such as, for example, begin ECG measurement, stop ECG measurement, analyze ECG measurements, transmit and receive ECG measurement data, and the like, and screening the patient for medical conditions, such as, for example, left ventricular ejection fraction ("LVEF"). The system 100 includes at least one ECG monitoring device 10A, a network 30, a monitor (e.g., a system manager) computer (or computing device) 40, a hosted server (or computer) 50, and a database 60, all of which may be coupled to each other via communication links 20. For instance, the hosted server 50 and database 60 may be connected to each other and/or the network 30 via one or more communication links 20. The at least one ECG monitoring device 10A and the monitor computer 40 may be coupled to the network 30 via communication links 20. The at least one ECG monitoring device 10A may include, e.g. standard ECG machine to measure 12 lead ECG, electrode that measure 3-lead ECG, combination of 4 electrodes and 3 lead ECG with an additional 5$^{th}$ electrode (near or on chest) to measure 5 lead ECG, holter monitor test, cardiac event recorder, cardiac loop recorder, implantable loop recorder, stress ECG, wearable device such as smart watch with heart monitoring capability/function, and the like. Furthermore, the at least one monitoring device 10A, the monitor computer 40, the hosted server 50, and the database 60 may each include a controller that carries out the method as disclosed herein.

The at least one ECG monitoring device 10A may be used by, for example, an authorized user (e.g., doctor, nurse, or the like) of a patient to whom the at least one ECG monitoring device 10A is being used. Once the at least one ECG monitoring device 10A collects ECG data from the patient, said data may then transferred immediately (or simultaneously with the data collection) to the monitor computer 40, the hosted server 50, or the database 60 for screening (or analysis) to detect medical conditions in otherwise asymptomatic patient.

The at least one ECG device 10A, the monitor computer 40, the hosted server 50, and the database 60 may each include a computer-readable medium including a computer program that may be executed to carry out the processes disclosed herein. The computer-readable medium may include a code section or code segment for performing each step disclosed herein.

Such code may include algorithm to screen asymptomatic patients for severely depressed LVEF (≤35%) using only ECG data. The algorithm could identify patients as candidates for the primary prevention treatment of an implantable defibrillator (ICD). The algorithm may include at least one of: probability algorithm, machine learning algorithm, or combination thereof.

In an embodiment of the present disclosure, the algorithm may analyze an ECG signal, such as, for example, 12-lead, 3-lead, 5-lead, or any combination thereof, for specific abnormalities using a step-wise logistical regression. For each abnormality identified in a patient, an additional point may be assigned to an electrical surrogate "ES" score to predict LVEF ≤35%. Heart rate abnormalities tested may include at least one or combination of the following:

Elevated resting Heart rate
Global P-wave duration
PR interval
QRS duration
QTc interval
QRS-T angle
Intrinsicoid deflection
QRS transition zone
T-peak to T-end-interval
Left ventricular hypertrophy

EXAMPLE 1

Hypothesis:
The collective presence of specific abnormal 12-lead ECG markers correlates with severely reduced LV ejection fraction (LVEF).

Methods:
A pooled analysis of prospectively identified sudden cardiac arrest (SCA) cases and geographical controls (69% with coronary disease) was performed from an ongoing community-based study in the US Northwest (catchment population approx. 1 million). Subjects were required to have archived 12-lead ECG and echocardiography data available. LVEF was determined from echocardiography reports, and archived ECGs were evaluated for elevated resting heart rate >75 bpm, left ventricular hypertrophy, delayed QRS transition zone, QRS-T angle >90°, prolonged QTc (>450 ms in men; >460 in women), and prolonged T-peak to T-end >89 ms. The ECG parameters were dichotomized as shown in, e.g., Table 1 below.

TABLE 1

|  | EF ≤ 35%<br>N = 85 | EF > 35%<br>N = 476 | p-value |
|---|---|---|---|
| DEMOGRAPHICS |  |  |  |
| Male | 74% | 63% | 0.04 |
| Age | 66.3 ± 14.7 | 66.5 ± 12.5 | 0.90 |
| EGG PARAMETERS |  |  |  |
| Heart Rate > 75 bpm | 54% | 34% | <0.001 |
| QTc prolonged* | 55% | 34% | <0.001 |
| Tpeak-Tend > 89 | 29% | 32% | 0.70 |
| QRS-T angle > 90° | 64% | 23% | <0.001 |
| QRS transition zone markedly delayed† | 65% | 23% | <0.001 |
| LVH by ECG criteria‡ | 26% | 14% | 0.005 |

Figure 2:
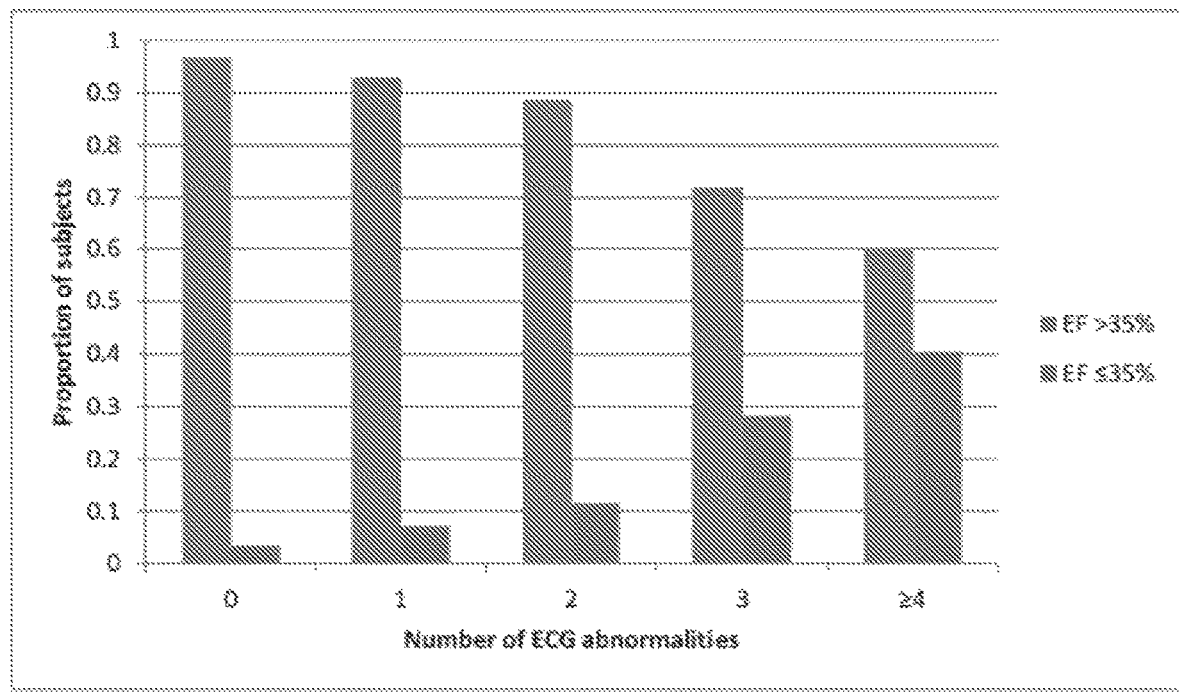
FIG. 2 illustrates a graph of an example of a number of ECG abnormalities detected using the algorithm that is constructed in accordance with the principles of the present disclosure.

*Prolonged QTc > 450 ms for men. > 460 ms for women
†QRS transition zone beyond V₄
‡Sokolow-Lyon or Cornell voltage criteria Results:

561 patients were included in the analysis (mean age 66.5±12.8, 65% male). 53% of the subjects with EF >35% (n=476) had 0-1 ECG abnormalities, compared to 18% in the group with low EF ≤35% (n=85). Conversely, 34% of subjects with low EF had ≥4 ECG abnormalities, compared to 9% among subjects with EF >35% (p<0.001). The proportion of subjects with EF ≤35% or EF >35% corresponding to the number of ECG abnormalities is presented in FIG. 2. Among subjects with ≤2 ECG abnormalities, fewer than 15% had EF ≤35%. Among subjects with 4 or more ECG abnormalities, 40% had EF ≤35%. The results are shown in FIG. 2 and Table 2 below.

TABLE 2

| Number of<br>abnormal<br>ECG markers | EF ≤ 35%<br>N = 85 | EF ≥ 35%<br>N = 476 |
|---|---|---|
| 0 | 5% | 23% |
| 1 | 13% | 30% |
| 2 | 16% | 23% |
| 3 | 32% | 15% |
| ≥4 | 34% | 9% |

Conclusions: The presence of specific ECG abnormalities was collectively associated with identification of severely reduced LV systolic function among patients with a high coronary disease burden. These findings may improve the effectiveness of screening for deployment of SCA primary prevention in the community.

EXAMPLE 2

Background:

It was previously reported that there is a significant underutilization of the primary prevention implantable defibrillator (ICD) in a segment of the general population, due to low prevalence of echocardiographic screening for reduced LVEF. Novel, noninvasive and cost effective methods, as disclosed herein, could enhance the screening process to identify appropriate candidates.

Objective:

To develop a 12 lead ECG based algorithm for improved identification of individuals with severely reduced LVEF.

Methods:

In a discovery population, among patients in an ongoing community based study of SCD in the Northwest US (2002-2015), it was determined that a combination of ECG parameters could predict echocardiographically-assessed LVEF ≤35%. In a separate validation population of both inpatients and outpatients in a southern California medical center with echocardiogram performed during 2015, those with a digital ECG obtained close to the echocardiogram (±14 days) were included. A stepwise logistic regression with 9 electrical ECG markers was used as predictors of EF ≤35%: heart rate, global P-wave duration, PR interval, QRS duration, QTc interval, QRST angle, intrinsicoid deflection, QRS transition zone, and LVH. Markers significant (p<0.10) in the final model were assigned one point in an electrical surrogate "ES" score to predict LVEF ≤35%. The ES score's test characteristics was evaluated including positive and negative predictive value (PPV and NPV) in the validation population.

Results: In the validation population (n=7601, 6.1% with LVEF ≤35%), elevated heart rate, prolonged QRS duration and QTc interval, wide QRS-T angle, delayed QRS transition zone, and delayed intrinsicoid deflection were significant predictors of LVEF ≤35%. The "ES" score ranged from 0 to ≥5 and showed a strong dose-response association with likelihood of LVEF ≤35%. Among the 7.4% of total patients with an ES score of ≥4, 32% had LVEF ≤35%. Using ≥4 abnormal ECG markers as a high-risk cutpoint resulted in a PPV of 0.326 and an NPV of 0.961.

Conclusions:

In both a discovery and a validation population, a novel ECG-based algorithm correlated strongly with severely reduced LVEF. These findings could have significant implications for improved, appropriate utilization of the primary prevention ICD.

As shown in, e.g., FIG. 2, the presence of specific ECG abnormalities was collectively associated with identification of severely reduced LV systolic function among patients with a high coronary disease burden.

Figure 3:
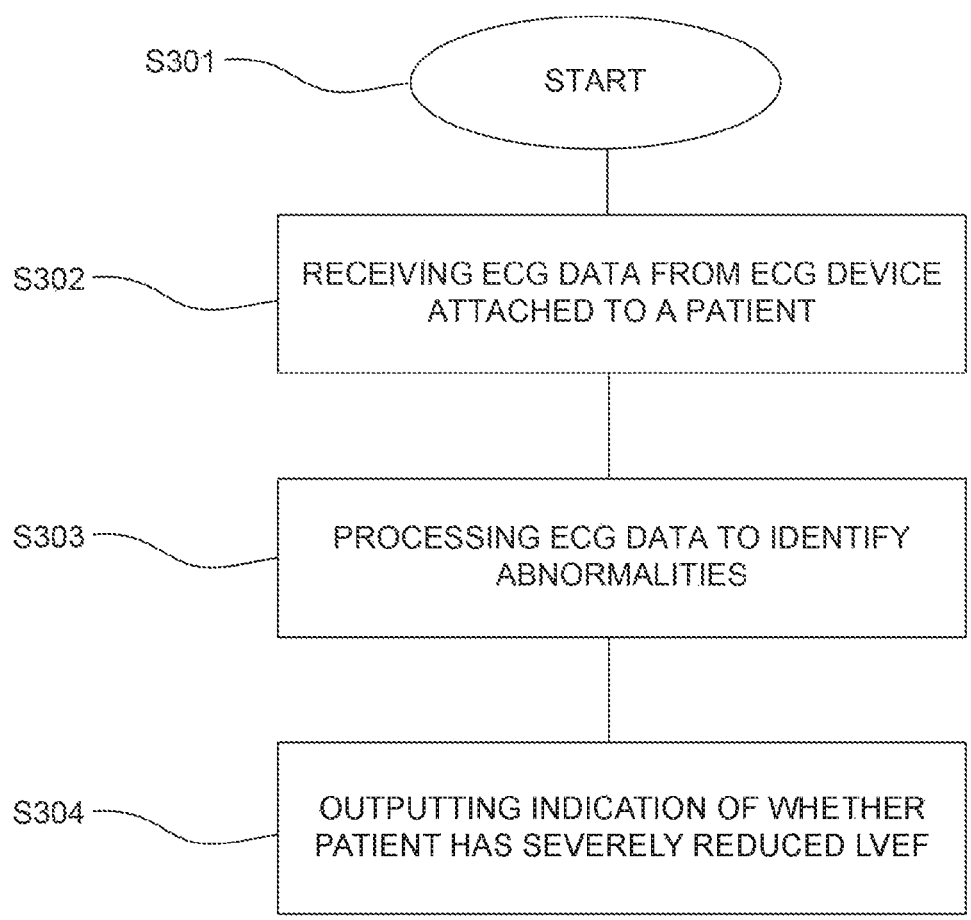
FIG. 3 illustrates, in accordance with various embodiments of the present invention, a flowchart of an example of a method for screening and detecting asymptomatic patients for severally depressed LVEF using only ECG (or EKG) data.

FIG. 3 discloses an example of a method of screening and detecting asymptomatic patients for severally depressed LVEF using only ECG (or EKG) data that is constructed in accordance with the principles of the present disclosure. The method includes: receiving, at a controller, ECG data from a ECG device attached to a patient (Step 301); processing, by the controller, the ECG data to identify abnormalities (Step 302); and outputting an indication of whether the patient has LVEF (Step 303). The controller may be on a separate computer system as disclosed in, e.g., FIG. 1. It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A system for identifying a patient with electrocardiogram (ECG) abnormalities comprising:
    an ECG monitoring device;
    a server;
    a database;
    a memory containing machine readable medium comprising a machine executable code having stored thereon instructions for analyzing ECG data; and
    a processor coupled to the memory, the processor configured to execute the machine executable code to cause the processor to:
        receive an ECG data output from the ECG monitoring device;
        process the ECG data output to identify abnormalities in any combination of ECG parameters selected from at least: a resting heart rate, a global P-wave duration, a PR interval, a QRS duration, a QTc interval, a QRS-T angle, an intrinsicoid deflection, a QRS transition zone, a T-peak to T-end interval, and a left ventricular hypertrophy amount; and
        analyze the abnormalities in the ECG parameters to determine whether the patient has at least a threshold number of abnormal ECG parameters,
    wherein the ECG monitoring device, the server, the database, the memory, and the processor are coupled to a network via communication links,
    wherein having at least the threshold number of abnormal ECG parameters indicates that the patient has reduced left ventricular ejection fraction (LVEF).

2. The system of claim 1, wherein the ECG monitoring device comprises at least one of: a ECG machine to measure 12 lead ECG, an electrode that measures 3-lead ECG, combination of 4 electrodes and 3 lead ECG with an additional $5^{th}$ electrode located near or on the patient's chest to measure 5 lead ECG, a holter monitor test, a cardiac event recorder, a cardiac loop recorder, an implantable loop recorder, a stress ECG, a wearable device with heart monitoring capability, and a combination thereof.

3. The system of claim 1, wherein the processing of the ECG data output comprises converting a raw data into a processed data.

4. The system of claim 1, wherein analyzing the abnormalities in the ECG parameters comprises weighting certain abnormalities and outputting an abnormality score.

5. The system of claim 4, wherein the abnormalities in the ECG parameters are detected by measuring a value of each of the ECG parameters and determining whether the value of each of the ECG parameters meets a threshold value.

6. The system of claim 1, wherein the at least one ECG monitoring device is configured to be used by an authorized user of the patient to whom the at least one ECG monitoring device is being used.

7. The system of claim 1, wherein the at least one ECG monitoring device collects ECG data from the patient and transfers the collected ECG data to at least one of the following: the monitor computer, the hosted server, or the database for screening to detect reduced LVEF in the patient when the patient is otherwise asymptomatic.

8. The system of claim 1, wherein the at least one ECG device, the monitor computer, the hosted server, and the database are configured to each include a computer-readable medium including a computer program that may be executed to carry out the method comprising: collecting an ECG data output from the patient; processing the collected ECG data output to identify the abnormalities in the collected ECG data; and assign abnormality scores to the collected ECG data by comparing the collected ECG data to a predetermined or threshold measurement data for the abnormalities.

9. The system of claim 8, wherein the computer-readable medium is configured to comprise a code section or code segment for performing each step disclosed in claim 8.

10. The system of claim 9, wherein the code section or code segment comprises an algorithm to screen or analyze asymptomatic patients for severally depressed LVEF using only ECG data.

11. The system of claim 10, wherein the algorithm identifies patients as candidates for the primary prevention treatment of an implantable defibrillator (ICD).

12. The system of claim 10, wherein the algorithm comprises at least one of: probability algorithm, machine learning algorithm, and a combination thereof.

13. The system of claim 10, wherein the algorithm comprises a step-wise logistical regression to analyze a 12-lead ECG signal for specific abnormalities.

14. A method for identifying patients with electrocardiogram (ECG) abnormalities comprising:
    receiving, at a controller, ECG data from a ECG monitoring device on a patient;
    processing, by the controller, the ECG data to identify abnormalities in any combination of ECG parameters selected from at least: a resting heart rate, a global P-wave duration, a PR interval, a QRS duration, a QTc interval, a QRS-T angle, an intrinsicoid deflection, a QRS transition zone, a T-peak to T-end interval, and a left ventricular hypertrophy amount;
    analyzing the abnormalities in the ECG parameters to determine whether the patient has at least a threshold number of abnormal ECG parameters, wherein having at least the threshold number of abnormal ECG parameters indicates that the patient has reduced left ventricular ejection fraction (LVEF) and
    outputting an indication of whether the patient has reduced LVEF.

15. The method of claim 14, wherein the ECG monitoring device is connected to a network, at least one monitoring device, a network, a monitor computer, a hosted server, and a database via communication links, wherein the ECG monitoring device, the at least one monitoring device, the monitor computer, the hosted server, and the database each comprise the controller.

16. The method of claim 15, wherein the controller comprises a non-transitory machine readable medium having stored thereon instructions for performing a method comprising machine executable code which when executed by at least one machine, causes the machine to carry out the method of identifying patients with a threshold number of distinct ECG abnormalities.

17. The system of claim 1, wherein the threshold number of abnormal ECG parameters is four.

18. The system of claim 1, wherein the determination that the patient has reduced LVEF is based only on ECG data.

* * * * *